United States Patent

Anderson

[11] 4,032,970
[45] June 28, 1977

[54] DENTAL MASK

[76] Inventor: Nina M. Anderson, 5212 Cogswell Road, El Monte, Calif. 91732

[22] Filed: July 8, 1976

[21] Appl. No.: 703,455

[52] U.S. Cl. .................................. 358/93; 358/250
[51] Int. Cl.² ...................... H04N 5/64; H04N 5/72
[58] Field of Search .............. 358/250, 230, 88, 90, 358/91, 93, 3, 64, 103, 104; 313/475; 273/DIG. 28; 350/96 B, 145, 147, 174, 298; 340/380

[56] References Cited

UNITED STATES PATENTS

| | | | |
|---|---|---|---|
| 2,825,260 | 3/1958 | O'Brien | 313/475 |
| 3,059,519 | 10/1962 | Stanton | 358/250 |
| 3,091,661 | 5/1963 | Alimanestiano | 358/250 |
| 3,748,016 | 7/1973 | Rossire | 350/174 |
| 3,833,300 | 9/1974 | Rymes | 350/96 B |
| 3,945,716 | 3/1976 | Kinder | 350/174 |

Primary Examiner—John C. Martin
Attorney, Agent, or Firm—Jack D. Slobod

[57] ABSTRACT

A face mask for occupying the senses of a dental patient during dental work has an interior surface positioned to be viewed by the patient. A fiber optic bundle is carried at one end on the viewing surface and at its other end is butted against the front of a cathode ray tube driven by the video output signal from an audio-visual program source. The mask carries earphones fed by the audio output of the source.

1 Claim, 3 Drawing Figures

DENTAL MASK

FIELDS OF THE INVENTION

The present invention relates generally to a face mask for occupying the senses of sight and hearing of a dental patient during dental work. In its particular aspects the present invention relates to a face mask carrying earphones and having an interior surface for view by the patient which is fed by a fiber optic bundle.

BACKGROUND OF THE INVENTION

One source of anguish to a dental patient is the sight and sound of dental tools such as a drill. This is particularly disturbing to small children. While small children easily become engrossed in an audio-visual program, as from television, I am not aware of any prior suggestion of using this propensity to occupy the senses of children during dental work.

OBJECTS OF THE INVENTION

It is an object of the present invention to provide a device for occupying the senses of a dental patient during dental work with an entertaining audio visual program.

It is a further object of the present invention to provide a face mask having earphones and having an interior viewing surface fed by a flexible image transmission conduit.

SUMMARY OF THE INVENTION

Briefly, the aforementioned and other objects of the present invention are satisfied by providing a device for occupying the senses of a dental patient which comprises a face mask having an interior surface positioned to be viewed by the patient. The flexible fiber optic bundle is carried at one end on the surface and is coupled at its other end to a picture output surface of an audio-visual program source. The face mask also carries earphones fed by the audio output of the program source.

The device thus occupies the senses of sight and sound of the dental patient while dental work is performed.

Other objects, features and advantages of the present invention will become apparent upon perusal of the following detailed description of the preferred embodiment thereof when taken in conjunction with the appended drawing wherein.

DETAILED DESCRIPTION

Figure 1:
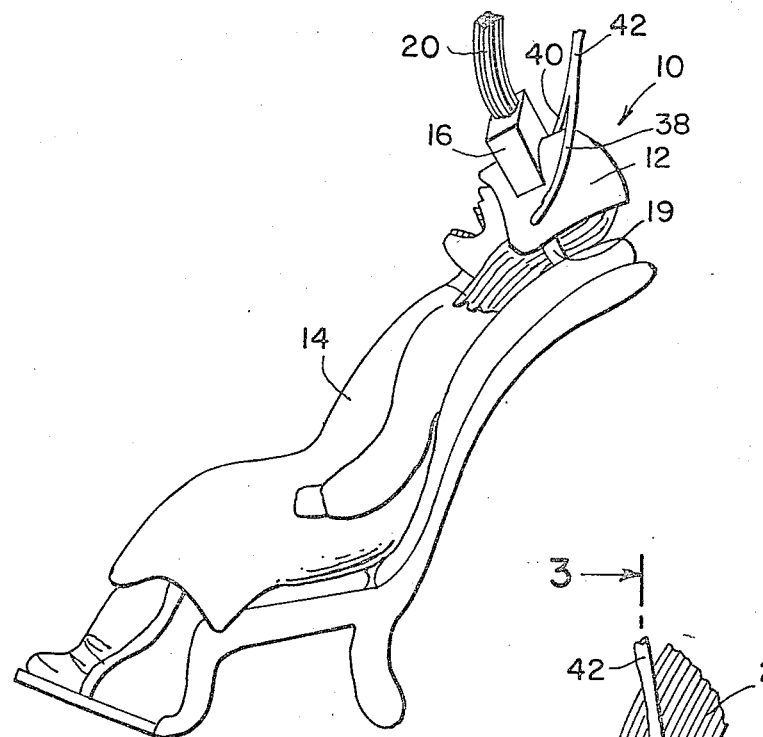
FIG. 1 is a generally elevational side view of the dental mask of the present invention as used by a dental patient.
Figure 2:
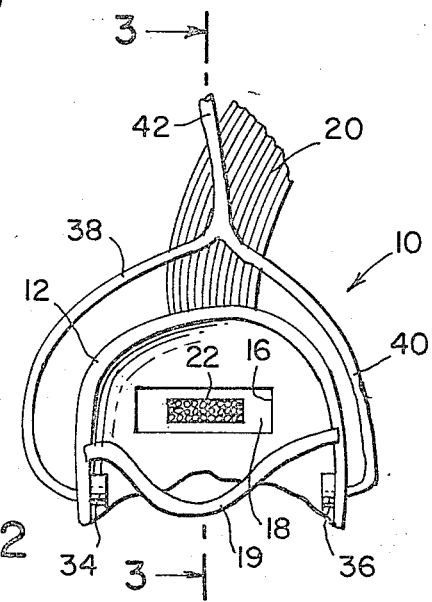
FIG. 2 is an elevational rear view of the mask in FIG. 1.
Figure 3:
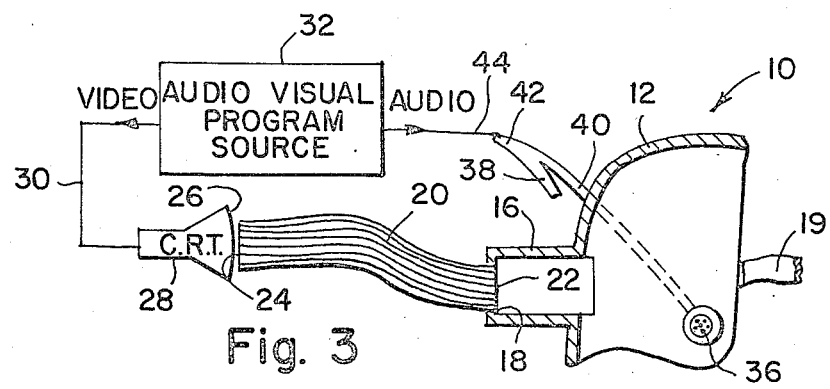
FIG. 3 is a cross-sectional side elevational view of the mask taken along the lines 3—3 in FIG. 2 with associated devices shown schematically.

Referring to FIGS. 1 through 3 of the drawing, the dental mask of the present invention is generally indicated by the reference numeral 10. Mask 10 comprises a rigid plastic molded mask body 12 proportioned to be over the eyes and ears of a dental patient 14. The mask body 12 includes an elongated rigid tubular tunnel 16 of rectangular cross-section projecting forwardly therefrom and carrying a rectangular interior surface 18 at its end which is spaced sufficiently from the eyes of patient 14, such as eight inches, in order to be viewed without eye strain. Mask body 12 is preferably open at its rear for slipping over the face of patient 14 and a strap 19 is provided at the back of mask 12 for engaging the back of the patients head.

A flexible fibre optic bundle 20, preferably of rectangular cross-section, has one end 22 forming a central portion of surface 18. The other end 24 of bundle 20 is butted against the face 26 of a cathode ray tube 28 which is appropriately master scanned and provided with a video input on line 30 from an audio visual program source 32 such as a television receiver or video tape player. Thus, the picture image on the tube face 26 is conveyed to surface 18 by fiber optic bundle 20.

Earphones 34 and 36 are carried by the sides of mask body 12 in position for covering the ears of patient 14 and branch cables 38 and 40 respectively emanating from earphones 34 and 36 are merged into a main cable 42 for feeding the earphones in parallel from the main cable. Main cable 42 is fed by the audio output of audio-visual source 32 on line 44. Consequently, the device 10 occupies the audio and visual senses of patient 14 while leaving the mouth of patient 14 exposed for dental work.

While the preferred embodiment of the present invention has been described and illustrated in specific detail, it should be understood that numerous modifications, additions and omissions in the details thereof are possible within the intended spirit and scope of the invention claimed herein.

What is claimed is:

1. A device for occupying the senses of a dental patient during dental work comprising:
   a face mask for covering the eyes of the patient, said face mask having an interior surface positioned to be viewed by the patient;
   a fiber optic image transmission bundle having one end carried by said surface;
   earphones carried by said face mask for covering the ears of the patient; and
   an audio visual program source having an audio signal output part for coupling to said earphones and a picture output surface for coupling to the other end of said fiber optic bundle.

* * * * *